(12) United States Patent
Ratsimbazafy et al.

(10) Patent No.: US 9,629,872 B2
(45) Date of Patent: Apr. 25, 2017

(54) SODIUM THIOSULPHATE FOR THE TREATMENT OF ECTOPIC CALCIFICATIONS

(71) Applicants: Institut National de la Sante et de la Recherche Medicale (INSERM), Paris (FR); Universite de Limoges, Limoges (FR); CHU de Limoges, Limoges (FR); Universite Paris-Sud 11, Orsay (FR)

(72) Inventors: Voa Ratsimbazafy, Limoges (FR); Jeremy Jost, Limoges (FR); Vincent Guigonis, Limoges (FR); Eric Caudron, Paris (FR)

(73) Assignees: INSERM (INSTITUT NATIONAL DE LA SANTE ET DE LA RECHERCHE MEDICALE), Paris (FR); UNIVERSITE DE LIMOGES, Limoges (FR); CHU DE LIMOGES, Limoges (FR); UNIVERSITE PARIS-SUD, Orsay (FR)

( * ) Notice: Subject to any disclaimer, the term of this patent is extended or adjusted under 35 U.S.C. 154(b) by 0 days.

(21) Appl. No.: 14/398,776

(22) PCT Filed: May 10, 2013

(86) PCT No.: PCT/EP2013/059744
§ 371 (c)(1),
(2) Date: Nov. 4, 2014

(87) PCT Pub. No.: WO2013/167741
PCT Pub. Date: Nov. 14, 2013

(65) Prior Publication Data
US 2015/0099013 A1   Apr. 9, 2015

(30) Foreign Application Priority Data

May 10, 2012   (EP) .................................... 12305517

(51) Int. Cl.
*A61K 33/04*   (2006.01)
*A61K 9/00*   (2006.01)
*A61K 9/107*   (2006.01)

(52) U.S. Cl.
CPC ............ *A61K 33/04* (2013.01); *A61K 9/0014* (2013.01); *A61K 9/107* (2013.01)

(58) Field of Classification Search
None
See application file for complete search history.

(56) References Cited

U.S. PATENT DOCUMENTS

| | | | | |
|---|---|---|---|---|
| 4,929,442 A | * | 5/1990 | Powell | ......................... 424/85.2 |
| 5,556,630 A | * | 9/1996 | Znaiden et al. | ............. 424/401 |
| 2002/0164381 A1 | | 11/2002 | Shacknai et al. | |
| 2011/0105435 A1 | * | 5/2011 | Kohler et al. | .................. 514/89 |

FOREIGN PATENT DOCUMENTS

| WO | 2009103069 A1 | 8/2009 |
|---|---|---|
| WO | 2011005841 A1 | 1/2011 |

OTHER PUBLICATIONS

Wolf, E. et al., "Topical Sodium Thiosulfate Therapy for Leg Ulcers With Dystrophic Calcification," Arch Dermatol. 2008; 144(12):1560-1562.*
C. Giachelli, "The Emerging Role of Phosphate in Vascular Calcification," Kidney Int. May 2009; 75(9): 890-897.*
Arabshahi et al., "Abatacept and Sodium Thiosulfate for Treatment of Recalcitrant Juvenile Dermatomyositis Complicated by Ulceration and Calcinosis," J Pediatr. Mar. 2012; 160(3):520-522.*
Meissner et al., "The hemodynamics and diagnosis of venous disease," J Vasc Surg 2007; 46:4S-24S.*
O'Neill et al., "Recent Progress in the Treatment of Vascular Calcification," Kidney Int. 2010; 78(12):1232-1239.*
Bhambri et al., "Calciphylaxis: A Review," Resident's Forum, Jul. 2008, vol. 1, No. 2, p. 38-41.*

* cited by examiner

*Primary Examiner* — Tracy Vivlemore
*Assistant Examiner* — Monica Shin
(74) *Attorney, Agent, or Firm* — Whitham, Curtis & Cook, P.C.

(57) ABSTRACT

The present invention relates to pharmaceutical compositions comprising sodium thiosulphate dispersed in a hydrophile-in-lipophile emulsion, and the use thereof for topical administration for the treatment of an ectopic calcification and/or of the consequences thereof in an individual, the sodium thiosulphate being in the form of a pharmaceutical composition comprising, in addition, a hydrophile-in-lipophile emulsion. The invention also relates to a method for preparing these pharmaceutical compositions.

16 Claims, No Drawings

SODIUM THIOSULPHATE FOR THE TREATMENT OF ECTOPIC CALCIFICATIONS

The present invention relates to pharmaceutical compositions comprising sodium thiosulphate dispersed in a hydrophile-in-lipophile emulsion, and the use thereof for topical administration for the treatment of an ectopic calcification and/or of the consequences thereof in an individual, the sodium thiosulphate being in the form of a pharmaceutical composition comprising, in addition, a hydrophile-in-lipophile emulsion. The invention also relates to a method for preparing these pharmaceutical compositions.

BACKGROUND OF THE INVENTION

Cutaneous and subcutaneous calcifications (in general referred to as ectopic calcifications) complicate numerous diseases. They may be classified into dystrophic, metastatic, idiopathic, or iatrogenic calcifications, or into calciphylaxis.

Dystrophic calcifications are the result of local tissue abnormalities and grow in spite of normal plasma calcium and phosphorus levels. The main diseases that may develop due to these calcifications are: connective tissue diseases (scleroderma, CREST syndrome, juvenile dermatomyositis, lupus), cutaneous and subcutaneous infections (panniculitis), skin tumours (in particular pilomatricoma), certain congenital diseases (Elher-Danlos disease, Werner's syndrome, pseudo xanthoma elasticum).

Metastatic calcifications are, in contrast, the result of a disorder of calcium and phosphate metabolism (hypercalcemia and/or hyperphosphatemia). All diseases that cause these disorders may therefore contribute to the development of calcifications.

Idiopathic calcifications occur without tissue lesions or disorders of calcium and phosphate metabolism. The main known diseases in this group are tumoral calcinosis, scrotal calcifications as well as sub-epidermal calcified nodules.

Iatroqenic calcifications can occur following the injection of calcium or para-aminosalycylic acid. They have also been described following the use of calcium chloride saturated electrodes.

Calciphylaxis corresponds to the calcification of small sized blood vessels and of the sub-cutaneous adipose tissue. Most of the time secondary to chronic renal failure, and often associated with abnormalities of calcium and phosphate metabolism, however, it remains a separate entity given its specific pathophysiology and its particular evolutionary modalities.

Beyond the abnormal nature and unsightliness of their presence, these calcifications may cause complications in terms of functional capability (limitation of range of motion and joint function), with respect to pain (very painful nature of some calcifications, particularly in calciphylaxis) or on the trophic level (ischemia and necrosis of the cutaneous and subcutaneous tissues) that may—by such means—lead to additional infectious complications.

Although a number of treatments have been tried and reported (bisphosphonates, calcium channel blockers, probenecid) for these cutaneous and subcutaneous calcifications, to date there is no existing curative treatment for which efficacy has been demonstrated with a sufficient level of proof.

Sodium thiosulfate has been approved in the United States as an antidote for cyanide poisoning, and in the prophylaxis of cisplatin nephrotoxicity. Several publications have suggested a potential effect of sodium thiosulfate for the treatment of ectopic calcifications, and in particular of calciphylaxis. In the context of its marketing authorisation as an antidote for cyanide and in most of the published cases, sodium thiosulfate was administered preferably by the intravenous route. Certain articles report its use by oral administration. There is growing interest in the possible use of sodium thiosulfate by way of a systemic therapy for the treatment of calcifications caused for example by urolithiasis, nephrocalcinosis, tumoral calcinosis, calciphylaxis, or nephrogenic fibrosing dermopathies.

However prevailing concerns remain with respect to potential systemic side effects with these systemic routes (digestive disorders, metabolic acidosis, general bone related consequences, etc).

There is also an existing concentrated lotion containing 25% of sodium thiosulfate for cutaneous application, combined with acetylsalicylic acid, known by the trade name Versiclear®, which is authorised in the United States and is indicated in the treatment of the pityriasis versicolor. The presence of propylene glycol and isopropyl alcohol should be noted in its excipients.

The topical use of sodium thiosulphate could be advantageous, in particular for treating ectopic calcifications.

Two articles report the effects of sodium thiosulfate administration by cutaneous route. The first case concerns a 41-year old woman, suffering from systemic erythematosus lupus and presenting livedo reticularis with ulcers in her shins, the lesions being complicated by an infection, and a dystrophic calcification (Wolf et al. Arch Dermatol 2008; 144: 1560-2). A cutaneous treatment with sodium thiosulfate was administered twice a week, the treatment regimen being carried out in the physician's practice with application of 10% sodium thiosulfate compresses before dressing. This treatment therapy was complemented with the application of a topical corticosteroid around the wound. In addition, on a daily basis, the patient applied acetic acid compresses prior to the dressing. Her treatment was supplemented with suitable oral antibiotics. After six months, the superficial calcifications were dissolved, while at the same time the pains had progressively abated and it had been possible to reduce the antibiotics. Three months later, almost complete re-epithelialisation had occurred over the wound regions such that the antibiotic therapy could be stopped.

The second article reports two other cases treated by the cutaneous route. The first case concerns a 74 year old woman, suffering from osteo-arthritis, multiple sclerosis and pseudo-hypoparathyroidism, and presenting an ulcer on the leg with cutaneous calcium deposits and fibrosis (Bair et al, J Drugs Dermatol 2011; 10: 1042-4). The patient received topical applications of sodium thiosulfate 25% in zinc oxide applied twice daily over the wound region and the surrounding skin. This treatment was accompanied by the use of elasticated bandages, facilitating compression and elevation of the leg. The condition of the wound had improved significantly after five weeks, with good re-epithelialisation, and it had completely healed after 15 weeks of continuous therapy. The second case concerns a 81 year old man, with high serum calcium levels, mild renal failure and a calcified ulcer brought on by dystrophic calcification in the leg. This patient received the same treatment as the previous patient and was completely healed after 12 weeks of therapy.

Both of these published articles show that the cutaneous administration of sodium thiosulphate makes it possible to treat ulcers of the leg accompanied by cutaneous dystrophic calcifications. However, these articles do not give precise details pertaining to the formulation of sodium thiosulfate.

There are two main hypotheses to explain the effectiveness of thiosulfate. The first hypothesis would be chelation of the calcium attached to the blood vessels, the product thereof, the highly soluble calcium thiosulfate is then eliminated through the kidneys. The second mechanism would involve the antioxidant property of sodium thiosulfate (which possesses two unpaired electrons), which contributes to the restoration of endothelial function and the production of the enzyme eNOS (endothelial nitric oxide synthase).

Other hypotheses may also be considered. The sodium thiosulphate molecule indeed possesses two unpaired electrons, which are available for reacting with the reactive oxygen species generated during the endothelial dysfuntion that accompanies calciphylaxis. The production of a physiological antioxidant, the glutathione (GSH γ-glutamyl-cysteinyl-glycine), was observed during this reaction. Sodium thiosulfate could also be the cause of the emission of $H_2S$, a neurovascular modulator gas, from a variety of reactions involving thiol compounds with enzymatic trans-sulfuration reactions from the endogenous substrate that L-cysteine represents. This molecule, $H_2S$, is known as being endowed with vasodilator, analgesic and anti-inflammatory properties that may explain the pain relief effects observed in all of the cases reported. The improvement of endothelial dysfunction may also explain the intense and rapid relief of neuropathic pains reported.

The chelating properties of sodium thiosulfate towards calcium would be responsible for its action on the subcutaneous calcifications that develop in the form of painful plaques or nodules, the action taking place over a long-term, requiring months of treatment, but the real occurrence of which is objectively demonstrated by physical examination (palpation) and imaging.

The inventors have developed a pharmaceutical composition comprising sodium thiosulfate dispersed in a hydrophile-in-lipophile emulsion. They have also administered this preparation by the cutaneous route to a 12 year old boy with a large sized subcutaneous calcification on the posterior surface of his left elbow, which limited the mobilisation of the elbow. The patient applied topically every evening about 1 to 1.5 gram of the pharmaceutical composition having a sodium thiosulfate content amounting to 10% (by weight). The patient received no other type of treatment during his treatment with sodium thiosulfate. After six months of treatment, the medical examination showed a dramatic improvement, with no visible subcutaneous lesion and the mobilisation of the elbow being restored to the normal state. In addition, no systemic or local side effect was observed. These data demonstrate that sodium thiosulfate can be used for topical administration as a means of providing an effective and safe treatment of soft tissue calcifications.

Consequently, the invention thus relates to the use of sodium thiosulfate intended for topical administration for the treatment of an ectopic calcification and/or of the consequences thereof in an individual, who may or may not be receiving any other preventive or therapeutic, pharmacological or mechanical medication for calcifications. The invention also relates to the pharmaceutical composition comprising sodium thiosulfate dispersed in a hydrophile-in-lipophile emulsion developed by the inventors, as well as the method for preparing this pharmaceutical composition.

DESCRIPTION OF THE INVENTION

Use of Sodium Thiosulfate for the Treatment of Ectopic Calcifications and/or the Consequences Thereof by Topical Administration The invention relates first of all to sodium thiosulfate for use for topical administration for the treatment of an ectopic calcification and/or of the consequences thereof in an individual, the sodium thiosulphate being in the form of a pharmaceutical composition comprising, in addition, a hydrophile-in-lipophile emulsion.

The term "sodium thiosulfate" refers to any compound having the anhydrous formula $Na_2S_2O_3$ or any compound commonly known by the following names: sodium thiosulfate, hyposulphate of sodium, disodium salt of thiosulfuric acid, sodium hyposulphate, natrii thiosulfas, sodium thiosulphate, natrium thiosulfuricum, natrium thiosulfat.

The sodium thiosulfate that is marketed is often a hydrate, generally pentahydrate $Na_2S_2O_3$, $5H_2O$ (CAS number 10102-17-7: IPCS, 1993). Having the empirical formula $H_{10}Na_2O_8S_2$, its molecular weight is 248.2. Sodium thiosulfate pentahydrate is a solid product that is present in the form of granules or crystals, which are colourless or white, and odorless. Slightly hygroscopic, it becomes deliquescent in humid atmosphere. Sodium thiosulfate pentahydrate melts at 45° C., dissolves in the crystallisation water thereof at about 49° C. and is very soluble in water, 780 g/l at 20° C. At 100° C., it loses its water molecules, and decomposes beyond that, releasing sulfur oxides and sodium oxide.

Sodium thiosulfate decomposes upon contact with acids by emitting toxic sulfur dioxide. It reacts with iodides, salts of mercury, silver, lead and other heavy metals as well as oxidising agents. Furthermore, it can explode on contact with strong oxidisers (chlorates, nitrates or permanganates).

Aqueous solutions decompose slowly, based on a reaction accelerated by acids, into $Na_2S_2O_3 \rightarrow Na_2SO_3+S$ and, accelerated in the presence of oxygen, into $Na_2S_2O_3+H_2O \rightarrow Na_2SO_4+H_2S$. Whereas the calculated pH of a saturated aqueous solution is 8.1, the solutions concentrated to 10% have a pH approaching neutral, between 6.0 and 8.4. The pKa1 is between 1.46 and 1.74. An injectable solution of 0.15 g/mL with added sodium phosphate dodecahydrate ($Na_2HPO_4.12H_2O$) at a concentration of 1.21% for its part has a pH between 8.2 and 8.8. Packaged in an ampoule, it is then stable for 3 years. These solutions decompose even more rapidly with heat. Sodium thiosulfate pentahydrate should be stored, while preventing contact with air and exposure to light, in a cool environment, away from acids and oxidising agents.

The "individual" to be treated is in particular a mammal, preferably a human. The individual may for example be an adult or a child. The individual may or may not be receiving any other preventive or therapeutic, pharmacological or mechanical medication for calcifications, in addition to the pharmaceutical composition according to the invention. According to a particular embodiment, the individual does not receive any other preventive or therapeutic, pharmacological or mechanical medication for calcifications, in addition to the pharmaceutical composition according to the invention.

By "topical administration" is understood any administration by the local route, for example over the skin, an orifice, or a mucous membrane. Topical administration as used herein, includes the cutaneous, aural, nasal, vaginal, urethral, and rectal routes of administration.

Sodium thiosulfate is formulated in a cream which is a pharmaceutical form that lends itself particularly well to a topical administration intended to obtain a local effect.

The inventors have reported that the administration by the topical route of a pharmaceutical composition comprising sodium thiosulfate and a hydrophile-in-lipophile emulsion, without being combined with any other treatments, allowed drastically reducing a large sized subcutaneous calcification on the elbow of a twelve year old boy suffering from a tumoral calcinosis syndrome. Consequently, a pharmaceutical composition comprising sodium thiosulfate and a hydrophile-in-lipophile emulsion may therefore be advantageously used via the topical route in order to treat an individual having one or more ectopic calcification(s). In addition, the pharmaceutical composition according to the invention can be used preferably alone, that is to say not in combination with other therapeutic treatments.

The term "ectopic calcification" refers to all pathological deposit of calcium salts or any bone growth in the tissues, in particular in a soft tissue or in any other location accessible to a treatment by topical administration. The term "soft tissue" refers to a tissue other than bone tissue, which connects, supports, or surrounds other structures and organs of the body. The soft tissues include the tendons, ligaments, the fascia, the skin, fibrous tissues, adipose tissues, synovial membranes, the muscles, nerves and blood vessels.

The skin has a structure consisting of three layers: the epidermis, the dermis and the hypodermis or subcutaneous tissue. The subcutaneous tissue contains the adipose and connective tissue that houses the large blood vessels and nerves. Most vascular and ectopic calcifications are located in the cutaneous and subcutaneous tissues. Moreover, these tissues are particularly easy to access so as to enable the topical administration of sodium thiosulfate. As a consequence, the calcification to be treated is preferably a cutaneous or subcutaneous calcification.

Sodium thiosulfate administered by the topical route can enable the treatment of any ectopic calcification, whatever its origin. In particular, the sodium thiosulfate can be used to treat metastatic, dystrophic, iatrogenic, or idiopathic calcifications, calcifications associated with calciphylaxis, or subcutaneous ectopic ossifications.

Sodium thiosulfate may be used preferably to treat calcifications associated with a disease or pathological condition selected from the group consisting of primary hyperparathyroidism, vitamin D intoxication, milk drinker's syndrome, hypercalcemia, secondary hyperparathyroidism, renal failure, hyperphosphatemia, in particular genetic hyperphosphatemia, scleroderma, dermatomyositis, in particular the juvenile form, mixed connective tissue diseases, lupus, CREST syndrome, Elhers-Danlos syndrome, pseudo xanthoma elasticum, Werner's syndrome, late cutaneous porphyria, pseudo hypoparathyroidism, pseudo pseudo-hypoparathyroidism, (primary or secondary) venous or arterial insufficiency, diabetes, scrotal calcinosis, ossifying myositis, post-traumatic ectopic ossifications and any other disease or pathological condition caused by calcium crystal deposit(s), in particular of hydroxyapatite or calcium pyrophosphate.

Sodium thiosulfate administered by the topical route may also be used to treat the consequences of ectopic calcification.

The term "consequences of ectopic calcification" refers to any complications related to the presence of an ectopic calcification. This type of complication may for example be a functional complication (in particular a limitation of range of motion and joint function), a pain, a trophic complication (in particular ischemia or necrosis of the cutaneous and/or subcutaneous tissues), or an infection.

In order to facilitating the topical administration of sodium thiosulfate and to facilitate its access to the site of the calcification to be treated, sodium thiosulfate is formulated in a pharmaceutical composition which further comprises a hydrophile-in-lipophile emulsion.

Pharmaceutical Compositions Comprising Sodium Thiosulfate

The pharmaceutical compositions to be used for implementing the treatment according to the invention contain sodium thiosulfate in an amount that is effective for achieving the desired goal. In addition, the pharmaceutical compositions used for the implementation of the treatment may contain suitable pharmaceutically acceptable carriers comprising excipients and adjuvants that facilitate the formulation of sodium thiosulfate in preparations which may be used pharmaceutically. The term "pharmaceutically acceptable" encompasses any carrier that does not negatively interfere with the effectiveness of the active ingredient on the calcifications or ossifications, and that is not toxic to the host to whom it is administered. In particular, pharmaceutically acceptable carriers that are suitable for a composition according to the invention are carriers that are particularly suitable for the application of the composition over the skin, an orifice, or a mucous membrane. Suitable pharmaceutically acceptable carriers are well known in the art and are described for example in Remington's Pharmaceutical Sciences (Mack Publishing Company, Easton, USA, 1985), a standard reference text in this field. Pharmaceutically acceptable carriers are selected in accordance with the topical mode of administration, and the solubility and the stability of sodium thiosulphate.

The pharmaceutical composition containing the sodium thiosulfate is formulated in the form of a cream.

Pharmaceutically acceptable carriers used in creams contain a hydrophile-in-lipophile (H/L) emulsion comprising a dispersed hydrophilic phase and a continuous lipophilic phase.

Another aspect of the present invention therefore relates to a pharmaceutical composition comprising sodium thiosulfate and a hydrophile-in-lipophile emulsion. In particular, the composition according to the invention may be a pharmaceutical composition comprising sodium thiosulfate and a water-in-oil emulsion.

An "emulsion" is a mixture, macroscopically homogenous but microscopically heterogeneous, of a lipophilic phase and a hydrophilic phase of immiscible liquids, such as water and an oil. One phase is dispersed in the second phase in the form of droplets. For a "hydrophile-in-lipophile type emulsion", the hydrophilic phase is dispersed in the lipophilic phase.

Preferably, the content by weight of sodium thiosulfate in the composition according to the invention is from 5% to 25% relative to the total weight of said composition. Even more preferably, the content by weight of sodium thiosulfate in the composition according to the invention is from 5% to 15%, in particular from 8% to 12%, or even from 9.5% to 10.5% relative to the total weight of said composition.

The doses are administered on the basis of the individual needs, the desired effect, the size and location of the calcification. It is understood that the dosage administered will be dependent upon the age, gender, health and weight of the recipient, as well as on a concurrent treatment therapy, if applicable, on the frequency of treatment, and the nature of the desired effect. The total dose required for each treatment may be administered in multiple doses or in one single dose. An indicative dose for the composition according to the invention may for example be about 1 to 1.5 gram to be applied locally on a daily basis, for example, every night and to be left to act throughout the night.

Preferably, the hydrophile-in-lipophile (H/L) emulsion according to the invention comprises of a hydrophilic component, a lipophilic component that is liquid at room temperature, and a lipophilic component that is solid at room temperature. The term "room temperature" is understood to refer to a temperature between 18° C. and 25° C.

The lipophilic component that is solid at room temperature preferably comprises a wax. The term "wax" refers to a compound that is solid or substantially solid at room temperature, and whose melting point is generally greater than 35° C. The waxes may be of animal, vegetable, mineral or synthetic origin.

The lipophilic component that is solid at room temperature may for example include beeswax, such as white wax and yellow wax, whale spermaceti, cetyl palmitate, carnauba wax, candelilla wax, ouricurry wax, Japan wax, cork fibre wax, or sugarcane wax, a paraffin wax, vaseline or petroleum jelly, a montan wax, a microcrystalline wax, lanolin wax, ozokerite or ceresin, a hydrogenated oil such as hydrogenated castor oil, a silicone wax, a vegetable wax (or a butter), a fatty alcohol that is solid at room temperature, a synthetic wax such as Fischer-Tropsch or polyethylene wax, or a mixture thereof.

The content by weight of each of the components comprised in the composition according to the invention may vary. Preferably, the lipophilic component that is solid at room temperature is present at a content by weight of 5% to 28%, preferably from 8% to 25%, even more preferably from 10% to 23%, relative to the total weight of said composition.

Furthermore, the ratio by weight of the lipophilic component that is liquid at room temperature to that of the hydrophilic component that is liquid at room temperature is preferably from 0.8 to 1.9, preferably from 1 to 1.9, preferably from 1.1 to 1.8, and even more preferably from 1.15 to 1.75. In a preferential manner, the ratio by weight of the lipophilic component that is liquid at room temperature to that of the hydrophilic component that is liquid at room temperature is from 1 to 1.9 when the pharmaceutical composition is to be used for a child. It may vary from 0.8 to 1.9 when the pharmaceutical composition is to be used for an adult.

The term "liquid lipophilic component" refers to a substance composed of identical or different molecules, having hydrophobic properties, and that is liquid at room temperature.

The liquid lipophilic component may in particular comprise an oil. The oils may be of vegetable, animal, mineral or synthetic origin.

The lipophilic component that is liquid at room temperature may for example comprise an animal oil such as mink oil, cod liver oil, or halibut liver oil, sea turtle oil, a mineral oil such as paraffin oil, a synthetic oil such as perhydrosqualene, fatty alcohols, fatty amides, fatty acids or fatty esters, 2-ethylphenyl benzoate, octyl palmitate, isopropyl lanolate, triglycerides, including those of capric/caprylic acid, dicaprylyl carbonate, ethoxylated or propoxylated fatty esters and ethers; silicone oils (cyclomethicone, polydimethylsiloxanes or PDMS) or fluorinated oils, and polyalkylenes, trialkyl trimellitates such as tridecyl trimellitate, a vegetable oil, or a mixture thereof. In a preferential manner, the lipophilic component that is liquid at room temperature according to the invention comprises at least one vegetable oil.

The term "vegetable" or "of vegetable origin" refers to a substance extracted or derived from one or more parts of one or more plants. This therefore excludes in particular the compounds derived from an animal.

The one or more vegetable oils of the invention are preferably selected from the group consisting of: oils of vegetable origin or a mixture of oils of vegetable origin, liquid triglycerides of fatty acids having 4 to 10 carbon atoms such as triglycerides of heptanoic or octanoic acids of vegetable origin, or sunflower oil, corn oil, soybean oil, marrow or squash seed oil, sesame oil, hazel nut oil, almond oil, apricot oil, sweet almond oil, macadamia oil, arara oil, coriander oil, castor oil, avocado oil, rose hip oil, rose hip fruit oil, grape seed oil, black currant oil, jojoba oil, olive oil, peanut oil, coconut oil, kernel oils; semi synthetic oils such as triglycerides of caprylic/capric acids of vegetable origin; jojoba oil, shea butter oil; linear alkanes of vegetable origin, preferably comprising from 7 to 14 carbon atoms, and any one of the mixtures thereof.

The "liquid hydrophilic component", in particular the "aqueous solution", may include water and possibly solvents and/or water-soluble additives. By way of water soluble solvents, mention may be made in particular of alcohols having from 2 to 8 carbon atoms, especially from 2 to 6 carbon atoms such as ethanol. By way of polyols, mention may be made, for example of glycerol, butylene glycol and polyethylene glycols. The aqueous phase may optionally contain other additives such as water-soluble active agents, preservatives, salts, gelling agents, fillers, water dispersible or water-soluble polymers, water soluble dyes, etc.

The "additives" according to the invention may for example be stabilisers, excipients, buffers, or preservatives. The solvents and/or water soluble additives optionally present in the hydrophilic component that is liquid at room temperature may for example be selected among gums, anionic, cationic, amphoteric, or nonionic surfactants, silicone surfactants, gums, resins, dispersing agents, semi crystalline polymers, hydrophilic structuring agents, antioxidants, preservatives, fragrances, neutralising agents, antiseptic agents, UV filters, cosmetic active agents, such as hydrophilic vitamins, moisturising agents, emollients or collagen protecting agents, and mixtures thereof.

Preferably, the invention relates to a pharmaceutical composition comprising sodium thiosulfate and a hydrophile-in-lipophile emulsion, wherein the emulsion comprises, by weight relative to the total weight of the emulsion: (i) 7%-30%, preferably 10%-25%, of a lipophilic component that is solid at room temperature; and (ii) 45%-65%, preferably 50%-60%, of a lipophilic component that is liquid at room temperature; and (iii) 15%-40%, and preferably 20%-35%, of a hydrophilic component that is liquid at room temperature.

Preferably, the lipophilic component that is solid at room temperature comprises a wax. Preferably, the lipophilic component that is liquid at room temperature comprises a vegetable oil. Preferably, the hydrophilic component that is liquid at room temperature comprises at least water, and optionally one or more solvents and/or water-soluble additives, in particular a fragrance.

In particular, the hydrophile-in-lipophile emulsion may be Galen's Wax or Cold Cream.

"Galen's Wax" is an emulsion used in particular as a base for the formulation of dermatological officinal preparations. The original formula contains beeswax (or white wax), oil of sweet almond, rose water, and sodium borate. An example of a possible formula for the Galen's Wax is provided here below:

White Beeswax 13 g
Sweet Almond Oil 53.5 g
Rose Water 33 g
Sodium Borate 0.5 g.

"Cold Cream" is another emulsion used as a base for the formulation of dermatological officinal preparations, the formula of which differs from that of Galen's Wax by the presence of whale spermaceti (or cetyl palmitate), of tincture of benzoin and of essence of rose. An example of a possible formula for the Cold Cream is provided here below:

White Beeswax 8 g
Whale Spermaceti or Cetyl Palmitate 16 g
Sweet Almond Oil 55 g
Rose Water 16 g
Essence of Rose 0.5 g
Tincture of Benzoin 4 g
Sodium Borate 0.5 g.

Thus, a more specific pharmaceutical composition according to the invention is a composition in which the content by weight of sodium thiosulfate is from 5% to 25%, in particular from 8% 15%, or from 8% to 12%, or even from 9.5% to 10.5%, relative to the total weight of said composition, and in which the hydrophile-in-lipophile emulsion is Galen's Wax or Cold Cream.

Method for Preparation of the Pharmaceutical Compositions According to the Invention A final aspect of the invention relates to a method for preparing a composition according to the invention, comprising a step of dispersion of the sodium thiosulfate in a hydrophile-in-lipophile emulsion, the sodium thiosulfate optionally having been previously dissolved in a hydrophilic solution.

The method for preparing a composition according to the invention preferably comprises a first step of reducing the sodium thiosulfate into a fine and homogeneous powder, for example by means of grinding or micronization. The powder thus obtained may at a subsequent stage be dispersed in a pharmaceutically acceptable carrier which is a hydrophile-in-lipophile emulsion.

According to a first embodiment, the sodium thiosulphate powder may be directly dispersed in the hydrophile-in-lipophile emulsion, for example by progressive mixing of the sodium thiosulfate powder and the hydrophile-in-lipophile emulsion, until a macroscopically and/or microscopically homogeneous product is obtained.

According to a second embodiment, the sodium thiosulfate powder obtained during the first step can be dissolved in a fraction of the hydrophilic component that is used in the composition of the pharmaceutically acceptable carrier in a second step, so as to obtain an aqueous solution containing the sodium thiosulfate. A third step then consists of mixing this aqueous solution containing the sodium thiosulfate with the remainder of the pharmaceutically acceptable carrier, that is to say with an emulsion containing the total lipophilic component that is used in the composition of the pharmaceutically acceptable carrier and the fraction of the hydrophilic component of the pharmaceutically acceptable carrier that is not used in the step of dissolution of the sodium thiosulfate.

In particular, according to this second embodiment, the method for preparing a composition according to the invention may comprise the steps consisting of:

1) grinding or micronizing the sodium thiosulfate until a fine and homogeneous powder is obtained;

2) melting the solid lipophilic component of the pharmaceutically acceptable carrier in the liquid lipophilic component of the pharmaceutically acceptable carrier, in order to obtain the total lipophilic component;

3) mixing the ingredients constituting the liquid hydrophilic component of the pharmaceutically acceptable carrier;

4) mixing together the total lipophilic component obtained in step 2) with a first fraction of the liquid hydrophilic component obtained in step 3) until a homogeneous mixture is obtained;

5) dissolving the sodium thiosulfate powder obtained in step 1) in a second fraction of the liquid hydrophilic component obtained in step 3), in order to obtain an aqueous solution c the sodium thiosulfate;

6) adding the aqueous solution containing the sodium thiosulfate obtained in step 5) to the mixture obtained in step 4), and mixing until a homogeneous pharmaceutical composition is obtained.

According to this second embodiment of the method for preparing a composition according to the invention, the hydrophilic component is separated into two fractions, called "first and second fractions". Steps 4) and 5) may be carried out in any order. Preferably, step 5) is carried out just prior to step 6), in order to limit the degradation of the sodium thiosulfate in the aqueous solution.

Alternatively, according to this second embodiment, the method for preparing a composition according the invention may comprise the steps that consist of:

1) grinding or micronizing the sodium thiosulfate until a fine and homogeneous powder is obtained;

2) melting the solid lipophilic component of the pharmaceutically acceptable carrier in the liquid lipophilic component of the pharmaceutically acceptable carrier, in order to obtain the total lipophilic component;

3) optionally, mixing a part of the ingredients constituting the liquid hydrophilic component of the pharmaceutically acceptable carrier;

4) mixing together the total lipophilic component obtained in step 2) with the liquid hydrophilic mixture obtained in step 3), or with one of the ingredients constituting the liquid hydrophilic component of the pharmaceutically acceptable carrier, until a homogeneous mixture is obtained;

5) dissolving the sodium thiosulfate powder obtained in step 1) in the ingredient(s) constituting the liquid hydrophilic component of the pharmaceutically acceptable carrier that was/were not used in step 4), in order to obtain an aqueous solution containing the sodium thiosulfate;

6) adding the aqueous solution containing the sodium thiosulfate obtained in step 5) to the mixture obtained in step 4), and mixing until a homogeneous pharmaceutical composition is obtained.

The homogeneity of the pharmaceutical composition obtained may be monitored and controlled for example by means of microscopy by assessing the size of the hydrophilic globules dispersed in the continuous lipophilic phase, as well as the number thereof in a visual field of a given dimension. Such control may also enable to ensure good reproducibility of the method for preparing the pharmaceutical composition according to the invention. Furthermore, the content of the active ingredient(s) may be controlled for example by means of high performance liquid chromatography. Finally, certain physical and chemical parameters can be controlled, for example the pH range within which the pharmaceutical composition according to the invention is located.

The pharmaceutical composition according to the invention may preferably be packaged in an internally varnished aluminum tube suitable for medicinal products for human use. Such packaging indeed makes it possible to limit contact of the pharmaceutical composition with the oxygen in the air (a factor of degradation of sodium thiosulfate), as well as microbial contamination during use. The tube will then be preferentially stored in a cool and dry place, away from acids and oxidising substances.

EXAMPLE 1

Materials and Method

A series of formulations containing increasing concentrations of sodium thiosulfate (5%, 10%, 15%, 20% and 25%) was prepared (see Table 1). It was subsequently verified that the compositions prepared satisfied the following quality criteria: no release of sulfur odor, visual homogeneity and homogeneity when being spread.

TABLE 1

Composition of the formulations of sodium thiosulfate in a hydrophile-in-lipophile emulsion

| Name of the formulation | Ff5 | Fi10 | Ff10 | Ff15 | Ff20 | Ff25 |
|---|---|---|---|---|---|---|
| Sodium Thiosulfate | 5 | 10 | 10 | 15 | 20 | 25 |
| Hydrophilic/Lipophilic Emulsion | 95 | 90 | 90 | 85 | 80 | 75 |
| Pourable Water | 0 | 6.67 | 0 | 0 | 0 | 0 |
| White Wax | 12.35 | 10.8329 | 11.7 | 11.05 | 10.4 | 9.75 |
| Sweet Almond Oil | 50.83 | 44.58 | 48.15 | 45.48 | 42.8 | 40.13 |
| Distilled Rose Water | 31.35 | 27.50 | 29.70 | 28.05 | 26.4 | 24.75 |
| Sodium Borate | 0.48 | 0.42 | 0.45 | 0.43 | 0.4 | 0.38 |
| Lipophilic Component/Hydrophilic Component | 63.18/36.83 | 55.41/44.59 | 59.85/40.15 | 56.53/43.48 | 53.2/46.8 | 49.88/50.13 |
| Liquid Hydrophilic Component/Liquid Lipophilic Component | 36.83/50.83 | 44.59/44.58 | 40.15/48.15 | 43.48/45.48 | 46.8/42.8 | 50.13/40.13 |
| Ratio Liquid Lipophilic Component/Liquid Hydrophilic Component | 1.38 | 1.00 | 1.20 | 1.05 | 0.91 | 0.80 |

EXAMPLE 2

A boy aged 12 years suffering from a syndrome of familial tumoral calcinosis presented with a significantly sized subcutaneous calcification on the posterior surface of his left elbow. The size of the calcification resulted in a reduction of the mobilisation of the elbow. Given the functional impairment and potential limitations of a surgical intervention, it was decided to administer a percutaneous treatment with sodium thiosulfate. The preparation consisted of sodium thiosulfate dispersed in a lipophilic base (10/90, weight/weight) (formulation denoted as "Fi10" in Table 1). The child did not receive any other type of mechanical or pharmacological medication.

The patient applied locally about 1 to 1.5 gram of the treatment product every evening and let it act throughout the night. No side effect, either systemic or local, have been reported or observed. After six months of treatment, the medical examination confirmed a dramatic improvement, with no visible subcutaneous lesion and the mobilisation of the elbow being restored to the normal state. An X-ray analysis further confirmed the improvement.

Sodium thiosulfate is a promising agent for the treatment of subcutaneous calcifications. Published papers pertaining to the intravenous administration of sodium thiosulfate have reported promising results. However, concerns with respect to safety remain with regard to the systemic administration of sodium thiosulphate due to digestive, metabolic, and bone related side effects. As a consequence, a topical application of sodium thiosulphate could offer a combination of the efficacy of this treatment with fewer or no systemic side effects. Two published articles report cases of successful treatments for microscopic dystrophic calcifications with sodium thiosulfate applied by the cutaneous route, but in both articles the treatment was combined with other medications. To the best of our knowledge, is herein described the first reported case of the disappearance of a subcutaneous metastatic calcification of a significant size following the topical administration of sodium thiosulfate, without the combination thereof with other treatments. The initial size of the calcification, the drastic improvement obtained, and the positive evolution over a relatively short period suggests that this evolution could not have been spontaneous.

These data show that sodium thiosulfate can be used in a topical administration to provide an effective and safe treatment, not only for subcutaneous metastatic calcifications, but also for all soft tissue calcifications, whatever the cause thereof, regardless of the mechanisms involved.

EXAMPLE 3

A 9 year old child, weighing 27 kg, suffering from progressive osseous heteroplasia presented with significant ossifications that were responsible for a limitation of function in the right foot: in the ankle region, with an estimated surface area of 10 cm×5 cm, and in the popliteal fossa area with 2 patches, having an estimated surface area of 6 cm×4 cm each. No improvement was observed in spite of a treatment with non steroidal anti-inflammatory medications and disodium etidronate. Taking advantage of a flare-up, a treatment with a composition according to the invention based on sodium thiosulfate dispersed at a 10% concentration in a hydrophilic/lipophilic emulsion was attempted (the formulation is denoted as "Ff10" in Table 1). The child did not receive any other type of mechanical or pharmacological medication.

In order to assess the efficacy of the treatment after 6 months, exploratory testing by imaging (computerised tomography or CT scanner) had notably been scheduled before treatment and after 6 months of treatment, and biological analyses in particular screening for methemoglobinemia. These exploratory tests were carried out in addition to the usual checkup including the exploration of renal function and liver function, as well as calcium and phosphate checkup.

After 3 months of treatment, the clinician had already noted greater mobility of the skin over the ossification.

From the point of view of efficacy of the treatment, the results after 6 months confirmed the non adhesion of the skin to the underlying ossification. In addition, cutaneous extrusions of calcium had totally disappeared. Finally, the scanner revealed that the size of ossifications had stabilised, whereas it had been an evolutionary process prior to the application of the topical treatment.

From the point of view of tolerance, no changes in renal function and liver function were observed, and methemoglobinemia was less than 1%.

These results further led to continue the treatment, with a higher concentration, of 15% (the formulation is denoted as "Ff15" in Table 1).

EXAMPLE 4

The third case concerns a 72 year old female patient suffering from a CREST type of scleroderma diagnosed over 15 years earlier. For a long time, she had digital calcifications that were complicated from time to time by ulcerations, and more recently, by confluent calcifications on the outer surface of both of her forearms. The usual general treatment of this patient combined prednisone 5 mg and bosentan. She did not receive any local treatment.

With the extension of the phenomenon of calcifications (appearance on the forearms) and the existence of a symmetry, the topical administration of a formulation according to the invention had been decided, at a concentration of 10% on one arm (the formulation is denoted as "Ff10" in Table 1) and a concentration of 25% on the other arm (the formulation is denoted as "Ff25" in Table 1).

After three months of treatment, the results show complete tolerance at both the concentrations. A "slight improvement" was noted by the patient, with a relatively higher intensity of the concentration at 25%.

The same type of assessments as those noted in Example 2 was set up after 6 months, suitably adapted for scleroderma.

EXAMPLE 5

Solutions of the following calcium salts were prepared by mixing one part of calcium powder into 30 parts of sterile pourable water: gluconate, chloride, carbonate, and monocalcium phosphates, dicalcium phosphates and tricalcium phosphates. The expected behaviours for these solutions were verified, in particular increasing water solubility when going from carbonate to chloride, and through the other salts.

One part of each formulation described in Example 1 is added to 10 parts of each of the previously prepared calcium solutions (PA x %/calcium salt). The duration of the contact with the pharmaceutical composition according to the invention being about 7 or 8 hours, the in vitro simulations are estimated at 4 hours for a stirring speed set at 60 rpm, at 2 hours for 120 rpm etc. The whole mixture is mixed at a speed of 120 rpm, for 2 hours with a Rayneri stirrer.

The effect of the formulations on the dissolution of the calcium salts is quantified by nephelometric and turbidimetric techniques. The greater the efficacy of the formulation in terms of dissolution of the calcium salt the lower is the turbidity thereof. Conversely, turbidity is high if the preparation has no effect on the calcium salt being studied.

Since certain mixtures do not respond in a satisfactory manner to these methods, spectrophotometry in the visible range is carried out. In order to obtain maximum sensitivity, the wavelength of an absorption peak is determined by scanning prior to carrying out the measurements of absorbance. Dilutions are made as far as necessary.

The measurements are accompanied by reference control solutions.

The invention claimed is:

1. A pharmaceutical composition comprising sodium thiosulfate and a hydrophile-in-lipophile emulsion, wherein the content by weight of sodium thiosulfate is from 5% to 25% relative to the total weight of said composition, and wherein the hydrophile-in-lipophile emulsion comprises a lipophilic component that is solid at room temperature, a lipophilic component that is liquid at room temperature, and a hydrophilic component that is liquid at room temperature, and wherein the lipophilic component that is solid at room temperature is present at a content by weight of 5% to 28% relative to the total weight of said composition.

2. A pharmaceutical composition according to claim 1, wherein the ratio by weight of the lipophilic component that is liquid at room temperature to that of the hydrophilic component that is liquid at room temperature is from 0.8 to 1.9.

3. A pharmaceutical composition according to claim 1, wherein the ratio by weight of the lipophilic component that is liquid at room temperature to that of the hydrophilic component that is liquid at room temperature is from 1 to 1.9.

4. A pharmaceutical composition comprising sodium thiosulfate and a hydrophile-in-lipophile emulsion, wherein the content by weight of sodium thiosulfate is from 5% to 25% relative to the total weight of said composition, and wherein the hydrophile-in-lipophile emulsion comprises a lipophilic component that is solid at room temperature, a lipophilic component that is liquid at room temperature, and a hydrophilic component that is liquid at room temperature, wherein the emulsion comprises, by weight relative to the total weight of the emulsion:
   a) 7%-30% of a lipophilic component that is solid at room temperature; and
   b) 45%-65% of a lipophilic component that is liquid at room temperature; and
   c) 15%-40% of a hydrophilic component that is liquid at room temperature.

5. A pharmaceutical composition according to claim 1, wherein said lipophilic component that is liquid at room temperature comprises at least one vegetable oil.

6. A pharmaceutical composition according to claim 1, wherein said hydrophilic component that is liquid at room temperature comprises water, and optionally one or more solvents and/or water soluble additives.

7. A pharmaceutical composition according to claim 1, wherein the content by weight of sodium thiosulfate is from 8% to 12% relative to the total weight of said composition, and wherein the hydrophile-in-lipophile emulsion comprises white beeswax, sweet almond oil, rose water, and sodium borate.

8. A method of treatment of an ectopic calcification and/or of the consequences thereof in an individual, said method comprising administering topically an effective amount of a pharmaceutical composition according to claim 1 to said individual, the sodium thiosulphate being in the form of a pharmaceutical composition comprising, in addition, a hydrophile-in-lipophile emulsion.

9. The method according to claim 8, the calcification being a cutaneous or subcutaneous calcification.

10. The method according to claim 8, the calcification being a metastatic calcification, a dystrophic calcification, a iatrogenic calcification, an idiopathic calcification, a calcification associated with calciphylaxis, or a subcutaneous ectopic ossification.

11. The method according to claim 8, the calcification being associated with a disease or pathological condition selected from the group consisting of primary hyperparathyroidism, vitamin D intoxication, milk drinker's syndrome, hypercalcemia, secondary hyperparathyroidism, renal failure, hyperphosphatemia, scleroderma, dermatomyositis, mixed connective tissue diseases, lupus, CREST syndrome, Elhers-Danlos syndrome, pseudo xanthoma elasticum, Werner's syndrome, late cutaneous porphyria, pseudo hypoparathyroidism, pseudo pseudo-hypoparathyroidism, venous or arterial insufficiency, diabetes, scrotal calcinosis, ossifying myositis, post-traumatic ectopic ossifications and any other disease or pathological condition caused by calcium crystal deposit(s).

12. A method for preparing a composition according to claim 1, comprising a step of dispersion of the sodium thiosulfate in a hydrophile-in-lipophile emulsion, the sodium thiosulfate having optionally been previously dissolved in a hydrophilic solution.

13. The method according to claim 11, wherein hyperphosphatemia is genetic hyperphosphatemia.

14. The method according to claim 11, wherein dermatomyositis is the juvenile form of dermatomyositis.

15. The method according to claim 11, wherein the venous or arterial insufficiency is primary or secondary.

16. The method according to claim 11, wherein the calcium crystal deposit(s) are hydroxyapatite or calcium pyrophosphate.

\* \* \* \* \*